US008475340B2

(12) United States Patent (10) Patent No.: US 8,475,340 B2
Maybaum (45) Date of Patent: Jul. 2, 2013

(54) HYPOXIC CONDITIONING IN PATIENTS WITH EXERCISE LIMITING CONDITIONS

(75) Inventor: Simon Maybaum, White Plains, NY (US)

(73) Assignee: Montefiore Medical Center, Bronx, NY (US)

( * ) Notice: Subject to any disclaimer, the term of this patent is extended or adjusted under 35 U.S.C. 154(b) by 473 days.

(21) Appl. No.: 12/657,997

(22) Filed: Jan. 29, 2010

(65) Prior Publication Data

US 2010/0137380 A1 Jun. 3, 2010

Related U.S. Application Data

(63) Continuation-in-part of application No. 12/157,870, filed on Jun. 13, 2008.

(60) Provisional application No. 60/961,863, filed on Jul. 25, 2007.

(51) Int. Cl.
*A63B 23/18* (2006.01)
*A63B 23/0244* (2006.01)
*A61M 2016/0006* (2006.01)
*A61B 5/087* (2006.01)
*A61B 5/0875* (2006.01)

(52) U.S. Cl.
USPC .......................................................... 482/13

(58) Field of Classification Search
USPC ............. 128/205.28, 202.12, 205.11, 205.12, 128/205.15, 205.26, 200.24; 482/13
See application file for complete search history.

(56) References Cited

U.S. PATENT DOCUMENTS

2005/0252512 A1 11/2005 Summers
2009/0025726 A1 1/2009 Maybaum

OTHER PUBLICATIONS

Rosalba Courtney, Intermittent Hypoxic Training, Feb.-Mar. 2001, International Wellbeing, Issue 83, pp. 1-4.*
Levine BD, Stray-Gundersen J.; "Living high-training low": effect of moderate altitude acclimatization with low altitude training on performance. Journal of American Physiological Society. 1997;83(1)102-112.
Nummela A. Rusko H.; Acclimatization to altitude and normoxic training improve 400-m running performance at sea level. Journal of Sports Sciences.2000; 18(6):411-9.
Rankovic G, Radovanovic D.: Physiological aspects of altitude training and the use of altitude simulators. Srpski Arhiv Za Celkupno Lekarstvo. 2005;.133(5-6):307-11. (Serbian abstract).
Heath D, Williams D.R.; High-Altitude Medicine and Pathology. 4th ed. New York, NY: Oxford Medical Publications; 1995:68.
Hultgren H.; High Altitude Medicine. Stanford California, Hultgren Publications: 1997.
Navot-Mintzer D., Epstein M., Constantini N.; Physical activity and training at high altitude. Harefuah. 142(10): 704-9, 2003(Abstract).

Liu Y.. Steinacker J.M., Dehnert C., Menold E., Baur S., Lormes W., Lehmann M.; Effect of "living high-training low" on the cardiac functions at sea level. International Journal of Sports Medicine. 1998;19(6):380-4.
Kolar F., Ostadal B.; Molecular Mechanisms of Cardiac Protection by Adaptation to Chronic Hypoxia. Physiological Research. 2004;53 Suppl 1:S3-13.
Strniskova M., Ravingerova T., Neckar J ., Kolar F., Pastorekova S., Barancik M.; Changes in the Expression and/or Activation of Regulatory Proteins in Rat Hearts Adapted to Chronic Hypoxia. General Physiology & Biophysics.2006; 25(1):25-41.
Varosian M.A., Kittnar O.E.; Prevention of heart failure by adapting the body to high-altitude hypoxia. Patologicheskaia Fiziologiia i Eksperimentalnaia Terapiia. 1991;(6):41-3 (Abstract).
Clark A.L., Poole-Wilson P.A., Coats A.J.S.; Exercise Limitation in Chronic Heart Failure: The Central Role of the Periphery. J Am Col Cardol 1996;28:1092-1102.
Mancini D.M., Henson D, LaManca J, Levine S; Evidence of reduced respiratory muscle endurance in patients with heart failure. J Am Coll Cardiol 1994;24:972-981.
Lipkin D, Jones D, Round J, Poole-Wilson P.; Abnormalities of skeletal muscle in patients with chronic heart failure. Int J Cardiol 1988;18:187-195. (Abstract).
Silverberg D.S., Wexler D., Blum M., Keren G., Sheps D., Leibovitch E., Brosh D., Laniado S., Schwartz D., Yachnin T., et al.; The Use of Subcutaneous Erythropoietin and Intravenous Iron for the Treatment of the Anemia of Severe, Resistant Congestive Heart Failure Improves Cardiac and Renal Function and Functional Cardiac Class, and Markedly Reduces Hospitalizations. Journal of the American College of Cardiology. 2000; 35(7): 1737-1744.
Mancini D.M., Katz S.D., Lang C.C., LaManca J., Hudaihed A., Androne A.S.; Effect of erythropoietin on exercise capacity in patients with moderate to severe chronic heart failure Circulation. 2003 ;107(2):294-9.
Agostoni P. Cattadori G., Guazzi M., Bussotti M., Conca C., Lomanto M., Marenzi G., Guazzi M.D.; Effects of Simulated Altitude-induced Hypoxia on Exercise Capacity in Patients with Chronic Heart Failure; American Journal of Medicine. 2000; 109(6):450-5.
Erdmann J., Sun K.T., Masar P., Niederhauser H.; Effects of Exposure to Altitude on Men with Coronary Artery Disease and Impaired Left Ventricular Function. American Journal of Cardiology. 81(3):266-70, 1998.
Bernheim A.; High altitude and cardiac disease. Schweiz Rundsch Med Prax.(German article) 2005;94(45):1760-4. (Abstract).

(Continued)

*Primary Examiner* — Manuel Mendez
*Assistant Examiner* — Pritesh Patel
(74) *Attorney, Agent, or Firm* — Irving M. Fishman

(57) ABSTRACT

Patients having exercise limiting conditions and those at risk of developing such conditions are exposed to a regimen of hypoxic conditions that simulate various altitude conditions. The exposure is of a temporary nature, being from a few hours to most of a day or night in any one day and repeated on a personally worked out regimen of from a series of consecutive days to a regular number of "on" and "off" days, to a random number of days. An alternate regimen is such exposure for a few minutes at a time followed by normoxic rest period of a few minutes, with the cycle repeated multiple times over the course of a treatment session. The conditioning treatment strengthens the cardiac tissue and skeletal muscle and the results extend beyond the treatment periods whereby the patient's condition is substantially improved.

23 Claims, No Drawings

OTHER PUBLICATIONS

Aerospace Medical Association Medical Guidelines Task Force, Alexndria, VA; Medical Guidelines for Airline Travel. 2nd edition. Aviation, Space, and Environmental Medicine. 2003; 74(5):A1-A17.
Devereux R, Reichek N.; Echocardiographic Determination of Left Ventricular Mass in Man: Anatomic Validation of the Method. Circulation 1977;55:613-618.
Kolias T, Aaronson K, Armstrong W.; Doppler-Derived dP/dt and −dP/dt Predict Survival in Congestive Heart Failure. JACC 2000;36(5):1594-99.
Steele B: Timed Walking Tests of Exercise Capacity in Chronic Cardiopulmonary Illness. J Cardiopulm Rehabil 1996;16:25-33.
Richalet J.P., Souberbielle J.C., and Antezana A.M.; Control of erythropoiesis in humans during prolonged exposure to the altitude of 6,542 m. Am J Physiol Regulatory Integrative Comp Physiol.1994; 266: R756-R764.
Ri-li Ge, S. Witkowski, Y. Zhang, C. Alfrey, M. Sivieri, T. Karlsen, G. K. Resaland, M. Harber, J. Stray-Gunderson, and D. D. Levine; Determinants of erythropoietin release in response to short-term hypobaric hypoxia J Appl Physiol 2002; 92: 2361-2367.
H Casas, M Casas, A Ricart, R Rama, J Ibáñez1, L Palacios, FA. Rodríguez, JL Ventura, G Viscor and T Pagés.; Effectiveness of Three Short Intermittent Hypobaric Hypoxia Protocols: Hematological Responses; Journal of Exercise Physiology.2000;3(2) 38-45.
B. D. Levine; Intermittent Hypoxic Training: Fact and Fancy. High Altitude Medicine & Biology 2002;3(2): 177-193.
Brugniaux J.V., Schmitt L., Robach P., Jeanvoine H., Zimmermann H., Nicolet G., Duvallet A., Fouillot J.P., Richalet J.P.; Living high—training low: tolerance and acclimatization in elite endurance athletes. European Journal of Applied Physiology. 2006; 96(1):66-77.
Pyne D.V., McDonald W.A., Morton D.S., Swigget J.P., Foster M., Sonnenfeld G., Smith J.A.; (2000) Inhibition of interferon, cytokine, and lymphocyte proliferative response in elite swimmers with altitude exposure. J Interferon Cytokine Res 20:411-41 (Abstract).
Groves B.M., Reeves J.T., Sutton J.R., Wagner P.D., Cymerman A., Malconian M.K., Rock P.B., Young P.M., Houston C.S.; Operation Everest II: elevated high-altitude pulmonary resistance unresponsive to oxygen. Journal of Applied Physiology. 1987;63(2):521-30.
Zielinski J.; Effects of intermittent hypoxia on pulmonary hemodynamics: animal models versus studies in humans. European Respiratory Journal. 25(1):173-80, 2005.
M. R. Miller, J. Hankinson, V. Brusasco, F. Burgos, R. Casaburi, A. Coates, R. Crapo, P. Enright, C. P. M. van der Grinten, P. Gustafsson, R. Jensen, D. C. Johnson, N. MacIntyre, R. McKay, D. Navajas, O. F. Pedersen, R. Pellegrino, G. Viegi, and J. Wanger; Standardisation of spirometry. Eur. Respir. J.2005; 26: 319-338.
Wilber et al; Operational Characteristics of a Normobaric Hypoxic System; Medicine & Science in Sports & Exercise: vol. 34 (5) Supplement May 1, 2002 p. 92.
Richardson, et al; Short-term effects of normobaric hypoxia on the human spleen; Eur J Appl Physiol; Online First: Nov. 28, 2007.
Yan B., et al; The effect of acute hypoxia on lift ventricular function during exercise; European Journal of Applied Physiology (2007) 100(3): 261-265.
Pedlar et al; Acute Sleep Responses in a Normobaric Hypoxic Tent; Medicine & Science in Sports & Exercise 37 (6); 1075-1079 (2005).
Basset, F.A., et al; Effects of short-term normobaric hypoxia on haematology, muscle phenotypes and physical performance in highly trained athletes; Experimental Physiology 91(2):391-402 (2006).
Kubler, W.; Exposure to altitude and cardiovascular diseases—Prt II: Compensatory and adaptive mechanisms; the European Cardiologist Journal by Fax Apr. 30, 2007; http://www.servier.com/pro/cardiologie/pdfs/kub76ang.asp.

Anand, I.S., et al; Syndromes of subacute mountin sickness; High Alt Med Biol 2004 Summer 5(2):156-170 (Abstract).
Bernardi, et al; Breathing patterns and cardiovascular autonomic modulation during hypoxia induced simulated altitude; Journal of Hypertension vol. 19(5) May 2001 947-958 (Abstract).
Section 5—Exercise Performance and Environmental Stress, Chapter 24, Exercise at Medium and High Altitude, p. 602-622.
Chouabe, et al; Reversibility of electrophysiological changes induced by chronic high-altitude hypoxia in adult rat heart; Am J Physiol Heart Circ Physiol 282:1452-1460, 2002.
Courtney; Intermittent Hypoxic Training; International Wellbeing, Issue 83, Feb.-Mar. 2001(4 pages).
Dietz, et al; Altitude Illness—Pulmonary Syndromes; e-medicine May 22, 2007, pp. 1-9; http://www.emedicine.com/emerg/topic795.htm.
Ri-Li Ge, et al; Curent concept of chronic mountain sickness: pulmonary hypertension-related high-altitude heart disease; Wilderand Environmental Medicine: vol. 12, No. 3, 190-194.
Green et al; normal skeletal muscle Na+—K+ pump concentration in patients with chronic heart failure; Muscle & Nerve, vol. 24, Issue 1, 69-76 (2001).
Harris, et al; High Alittude Medicine; American Fanily Physician Apr. 15, 998, vol. 57, No. 8, (10 oages).
Keyl, et al; Effects of breathing control on cardiocirculatory moulation in Caucasian lowlanders and Himalayan Sherpas; European Journal of Applied Physiology, vol. 83, No. 6, Dec. 2000, 481-488 (Abstract).
Maggiorini, et al; High-altitude pulmonary hypertension: a pathophysioloogical entity to different diseases; Eur Respir J 2003;22:1019-1025.
Shlim, David; High Altitude medical Advise for Travelers Treatment ofAltitude Illness; http://www.ciwec-clinic.com/altitude/alti4.html;1997 (7 pages).
Short, B.; The major health implications of ascent to high altitude; ADF Health vol. 1, Nov. 25, 1999, 18-23.
Vij, et al;Acclimatizationto Oxidative Stress at High Altitude; High Altitude Medicine & Biology, 6(4):301, 2005 (Abstract).
Wahrenberger; High Altitude and the Heart; Dartmouth-HitchcockMedical Center; http://www.dartmouth.edu/~cardio/Providers/topics/misc/altitude.html2006.
Wilber, et al; Effect of F(1)O(2) on physiological responses and cycling performance at moderate altitude; Medicine & Science in Sprots & Exercise 35(7):1153-1159,2003 (Abstract).
Yamauchi-Takihara,et al; Hypoxic Stress Induces Cardiac Myocyte-Derived Interleukin-6; Circulation 1995, 91:1520-1524.
Basnyat et al; Efficacy of Low-dose Acetazolamide(125 mg BID) for the Prophylaxis of Acute Mountain Sickness: A Prospective, Double-blind, Randomized, Placebo-controlledTrial; High Alltitue Medicine & Biology vol. 4, No. 1, 2003, 45-52.
Jonk et al; Effect of Acetazolamideon pulmonary and muscle gas exchange during normoxic and hypoxic exercise; J. Physiol 579.3 (2007) pp. 909-921.
Basnyat et al; Acetazolamide 125 mg BD Is Not Significantly Different from 275 mg BD in the Prevention of Acute Mountain Sickness: The Prophylactic Acetazolamide Dosage Comparison for Efficacy (PACE) Trial; High Altitude Medicine & Biology, vol. 7, No. 1, 2006, 17-27.
Schoene; Illness at High Altitude: CHEST 2008; 134:402-416.
Tissot van Patot, et al; Prophylactic Low-Dose Acetazolamide Reduces the Incidence and Severity of Acute Mountain Sickness; High Altitude medicine & Biology, vol. 9, No. 4, 2008, 289-293.

* cited by examiner

HYPOXIC CONDITIONING IN PATIENTS WITH EXERCISE LIMITING CONDITIONS

CROSS-REFERENCE TO RELATED APPLICATIONS

This application is a continuation-in-part of U.S. patent application Ser. No. 12/157,870, filed Jun. 13, 2008, which claims benefit of U.S. provisional Application Ser. No. 60/961,863, filed Jul. 25, 2007.

STATEMENT REGARDING FEDERALLY SPONSORED RESEARCH OR DEVELOPMENT

Not Applicable

FIELD OF THE INVENTION

The present invention relates to the field of treatment of heart disease patients and those at risk of developing heart disease, as well as other conditions having associated exercise limitations. It also relates to those patients with or at risk of developing heart failure (inclusive of systolic and/or diastolic heart failure) and or cardiomyopathy. It further relates to exercise training in subjects having conditions which otherwise limit exercise tolerance.

BACKGROUND OF THE INVENTION

Training at altitude is a method widely used by athletes to enhance their endurance and performance at sea level (1). Studies in the athletic literature suggest that simulated altitude exposure, utilizing hypoxic devices, may have a similar benefit (2, 3). The improved performance achieved by altitude exposure is thought to be due to the physiological changes that occur during acclimatization (1).

Several physiological changes occur during ascent to altitude from sea level. These changes are primarily due to the reduced partial pressure of inspired oxygen secondary to changes in barometric pressure with altitude (4, 5). Physiological changes with altitude usually appear above 2300-2800 meters (6). Within minutes of ascent to an altitude, circulatory and respiratory changes occur (4). Continued stay at the higher altitude leads to acclimatization, a process of physiological adjustment leading to adaptation to the changed altitude.

Studies in athletes suggest that improved exercise capacity with altitude exposure may be due to the changes in blood volumes and oxygen handling capacity of the red blood cells. During acclimatization, there is an erythropoietin induced increase in red blood cell mass in response to hypoxia. In addition, there is a rightward shift of the oxy-hemoglobin dissociation curve with increase in 2, 3-diphospoglycerate level. Right shift of the curve leads to reduced affinity for oxygen, and hence, improved tissue oxygenation (4).

Ventilatory changes also occur in response to acclimatization. There is an increase in ventilation, mainly due to an increase in tidal volume. This hypoxic ventilatory response also improves oxygen transportation (4). Furthermore, biochemical and structural changes in skeletal muscle occur and an increase in capillary density is found after exposure to high altitude. (4).

Altitude exposure may have a favorable effect on cardiac function as well. An interesting study by Liu et al, showed improvement in left ventricular and systolic diameter and stroke volume in a group of altitude trained athletes (7). Altitude induced hypoxia may lead to cardio protective effects against ischemic and reperfusion injury (8, 9). In another study, altitude adapted chinchilla rabbits showed activation of gene signaling that lead to prevention of hypertrophy in a pressure overload model (10).

Reduced exercise capacity is a dominant finding in heart failure. Several structural and functional abnormalities have been shown in skeletal muscle in patients with end stage heart failure, which may contribute to reduced exercise capacity (11, 12, 13). Heart failure is associated with impaired oxygen delivery to the periphery, and this may further contribute to impaired exercise capacity. Furthermore, increasing hemoglobin concentration has been shown to improve exercise capacity, which is likely related to improved oxygen delivery (14, 15).

Agostoni et al studied the acute effect of simulated altitude (up to 3000 m) on exercise capacity in heart failure patients. There was a reduction in exercise capacity during exercise at altitude for both normal subjects and those with heart failure. This acute exposure to altitude during the stress test was well tolerated in patients with advanced heart failure (peak $VO_2 < 15$ ml/kg/min) (16). Another study of patients with ischemic cardiomyopathy showed that acute exposure to altitude (2500 m) during exercise was well tolerated. In the prior two studies, there were no episodes of significant arrhythmia (17). Moreover, commercial airplane pressure conditions are equivalent to 2400 meters and airplane travel is considered safe for stable patients with heart failure (18, 19).

OBJECTS OF THE INVENTION

It is therefore an object of the invention to provide a means of obtaining beneficial physiologic changes in heart failure patients.

It is another project of the invention to provide a means of obtaining beneficial physiologic changes in oxygen handling in patents having cardiovascular conditions that include impaired oxygen handling and/or utilization.

Yet another object of the invention is to provide a means of prophylactic treatment of patients at risk of heart failure or other cardiovascular condition involving impaired oxygen handling and/or distribution.

Another object of the invention is to enhance recovery of exercise performance and/or slow and/or reverse deconditioning after surgical procedures.

Still another object of the invention is to provide beneficial skeletal and cardiac muscle effects in patients having conditions leading to exercise limitations and/or deconditioning.

An even further object of the invention is to provide a method of improving cardiac muscle in a patient having a cardiac disease or condition.

A still further object of the invention is to provide a means whereby a patient having a condition which limits exercise can resume an exercise regimen previously limited by that condition.

Another object of the invention is to provide a fitness regimen inclusive of an exercise component wherein the exercise component was previously limited due to a cardiovascular disease or condition.

Still other objects of the invention will be apparent to those of ordinary skill in the art.

BRIEF SUMMARY OF THE INVENTION

These and other objects of the invention can be achieved by exposing the patient in question to a regimen of hypoxic conditions that simulate various altitude conditions. The exposure is of a temporary nature, being from a few hours to most of a day or night in any one day and repeated on a personally worked out regimen of from a series of consecutive days to a regular number of "on" and "off" days, to a random number of days. An alternative regimen of the invention utilizes an "intermittent hypoxic training" in which the patient is exposed to very high altitude simulation for short periods (under 10 minutes) with short normoxia periods in which the high altitude, normoxia cycle is repeated a number of times over the treatment period, generally over a span of about 1-2 hours. Exercise training may (but need not) accompany the altitude exposure period, the normoxia period, or both.

BRIEF DESCRIPTION OF THE SEVERAL VIEWS OF THE DRAWING

Not Applicable

DETAILED DESCRIPTION OF THE INVENTION

The present invention is a method of treating patients having or disposed to having conditions which limit exercise, generally due to difficulties in cardiac function and/or oxygenation of cardiac tissues, although not specifically limited to such. More particularly, the invention is especially directed to treating patients having chronic heart failure or angina, most particularly to those patients having chronic heart failure. The invention is also directed to treating patients who are recognized as being of high risk of developing these conditions prior to symptoms of the these conditions becoming evident. The invention is also directed to patients having or at risk of developing cardiovascular disease more generally, but specifically those having or at risk of having systolic and/or diastolic heart failure. The invention further relates to conditioning effects on skeletal muscle function in those patients having skeletal muscle conditions which limit exercise capability such as muscular dystrophy. A significant proportion of muscular dystrophy patients also have associated cardiomyopathy and the present invention has positive effects in both aspects (skeletal muscle and cardiac muscle improvements in exercise tolerance and exercise performance in such patients).

The hypoxic conditions of the present invention can be a continuous hypoxic condition over the course of a single treatment (more than about 45 minutes) or intermittent short bouts of hypoxic conditions (not more than about 10 minutes) alternated with short bouts of normoxic conditions multiple times within a single treatment session. For ease of discussion, the "intermittent hypoxic conditions treatment" will hereinafter be referred to as IHT, while single hypoxic sessions that are longer than about 45 minutes and which are unbroken by normoxic periods will be referred to as "extended hypoxic conditions treatment" or "EHT". An EHT regimen may use alternation between two or more different hypoxic conditions for varying lengths of time within a single session as long as the various hypoxic conditions are all within the minimum limitations for EHT set out in the present invention as set forth below. EHT regimens include simulating conditions of at least 1500 m and generally not greater than about 5,500 m (however, the use of the intermittent variant between a base hypoxic level within the forgoing EHT elevation limits and short bouts of substantially higher elevations, including short bouts at elevations substantially beyond the upper limits indicated above for EHT, are also permissible and within the scope of EHT for the present invention. For the remainder of this discussion, the hypoxic conditions will be referenced to elevation in meters, where the oxygen content of the hypoxic air is that which is typical for ambient air at the designated number of meters above sea level. Although air density will vary with temperature, variations in temperature (and the resultant changes in air density) at a given elevation may be generally ignored, but if need be accounted for as a reference point, the reference temperature is one of an average mid-day temperature in mid spring at the given elevation. Alternatively, various hypoxic condition delivering devices are available on the market with settings based on elevation. In use of any of those devices, the elevation setting for the device may be relied on without reference to temperature. Treatments may be individualized as per the patient's ability to tolerate the hypoxic conditions. Usually, (other than the IHT regimen) treatments will be in the range of 1500 m to not greater than about 2700 m, with an initial treatment at 1500 m and elevation on subsequent treatments in intervals of about 200 m to about 300 m. Smaller or larger increments in elevation may be utilized as need be based on patient tolerability, such as 100 m, 200 m, 400 m, and 500 m. When referencing the IHT regimen, high altitudes are used for very brief periods. In these IHT regimens, altitude simulation is generally in the range in excess of 2,500 m, more preferably in excess of about 3,000 m, still more preferably in excess of about 3,500 m, yet more preferably in excess of about 4,000 m even more preferably in excess of about 5,000 m, still more preferably in excess of about 6,000 m, even more preferably in excess of about 7,500 m, still more preferably in excess of 8,000 m, yet more preferably in excess of 9,000 m, still more preferably in excess of 10,000 m. In individual cases, lower (but usually above 2,500 m) and higher (significantly above 10,000 m) simulated altitude can be used depending upon the individual patient, the patient's other conditions, and tolerability of the regimen. It should also be noted that benefit may also be had from using the IHT regimen using simulated elevations described in the EHT regimen above, although due to the lower elevations in the EHT than in the IHT regimens, fewer patients will gain substantial benefit from an IHT regimen at the lower elevations. Still, in patients particularly susceptible to hypoxic treatments, such treatment is deemed to be within the scope of the invention. Furthermore, because the IHT regimen suitable equipment is more flexible in terms of application and patient movement in normal activities (without any enclosure being required), the IHT method and/or equipment/devices may simply be more patient acceptable and more likely to result in compliance with recommended treatment protocols than the EHT regimen enclosure equipment/devices. Nonetheless, both IHT and EHT regimens are within the present invention, whether or not combined with an exercise regimen and if so combined, whether or not the exercise regimen is conducted during the hypoxia treatment or at other times in the day. It should also be noted that the IHT suitable devices are usually non-enclosure devices; they are generally masks. Thus, simply wearing the mask for the entire treatment session will accomplish the invention EHT variant without the need for an enclosure. An efficient manner of effecting an EHT regimen with intermittent exposure to even higher elevations can be achieved by repeatedly changing the settings on such a mask or by using such a mask inside of a hypoxic enclosure where the enclosure provides a base hypoxic condition and the mask can be worn and taken off periodically. While repeatedly changing settings on an enclosure device would be possible, the practicalities of doing so do not make that manner of achieving the IHT regimen reasonable for patients.

With respect to the EHT regimen, any one treatment on any one day can be begun at about 1 hour and increased gradually as treatments progress, however, treatments will most generally be at least about 1.5 hours, preferably at least about 2 hours, more preferably at least about 3 hours. The decision to increase time per treatment or elevation or both at one time and each of the rates of increase will depend on the patient's tolerability and the clinician's judgment concerning primarily the acute effects of the treatments. In general, the maximum treatment time per any one treatment is less than 24 hours, but if desired a continuous hypoxic environment for up to about 2 weeks can be maintained, if desired and tolerated. More preferably, the individual treatments will last no longer than about 20 hours, preferably no longer than about 18 hours, more preferably no longer than about 12 hours, still more preferably no longer than about 8-9 hours, yet more preferably no longer than about 6 hours, still more preferably no longer than about 4 hours. The above time of treatments are times spent in the hypoxic environment at the target elevation conditions or times spent in the hypoxic conditions above the minimum set forth and therefore includes time spent in raising and lowering the elevation between hypoxic points. In either case, the hypoxic condition treatment time does not include any time needed to bring the hypoxic air to the minimum set forth above or to return hypoxic conditions from that minimum to ambient conditions. Concerning the IHT regimen, the patient is exposed to the hypoxic condition selected for periods of about not more than about 10 minutes, preferably not more than about 7.5 minutes, more preferably not more than about 6 minutes, most preferably not more than about 5 minutes per intermittent interval. Each interval is followed by a normoxia period which is a sufficient for the patient time to adjust back to normoxic conditions. While the exact normoxic condition time frame between the "intermittent" hypoxic conditions is variable (depending on the individual being treated and his concurrent conditions), generally 2-5 minutes is suitable for the intervening normoxic interval. The "hypoxic/normoxic" cycle is repeated over a period of about 45 minutes to about 3 hours, preferably about 1 hour to about 2 hours, more preferably about 1 hour to 1.5 hours, and may be administered about 1-4 times over the waking day, preferably 1-2 times a day. Usually 16-30 sessions are satisfactory to show improvements, but fewer or more treatments are suitable as well.

Simulated altitude can be readily achieved using any of a number of hypoxic condition generating apparatuses. One commercially available system is a Colorado Altitude Training (CAT) portable enclosure system. This consists of a transparent enclosure and a CAT Air Unit that simulates altitude by reducing oxygen content in the air in the enclosure. Another is disclosed in US 2005/0252512. Another manufacturer of suitable devices for use in the present invention is HYPDXICO Altitude Training Systems. A device particularly suitable for the IHT regimen is Hypoxicator. Others are also commercially available and one of ordinary skill in the art (particularly in the Altitude Training art) will be able to select alternate equipment to accomplish the same result.

Air contains 20.9% oxygen, 78% nitrogen, and 1% trace gases (carbon dioxide and argon). Because these are relative amounts this composition is true both at sea level and at high altitude. As barometric pressure decreases with increasing elevation, the number of molecules in a given volume of air decreases proportionately. The result, on an absolute basis, is that there are fewer oxygen molecules present in air at higher elevations. The absolute number of nitrogen molecules also decreases at the same rate, so that the relative proportions of oxygen molecules in the air remains constant at 21% even though there are less molecules of oxygen in the air at high altitudes. CAT's simulation is accomplished using a high-flow hypoxic air delivery unit and a semi-sealed enclosure. The air unit draws in ambient room air and separates the oxygen molecules from the nitrogen molecules, creating the hypoxic or oxygen reduced air. This separation is done in a special filter called a molecular sieve bed. Molecular sieve beds are chambers filled with a naturally occurring tetrahedral substance called zeolite. When air is passed through a sieve bed under pressure, the oxygen molecules are trapped in the zeolite, while the nitrogen molecules are allowed to pass through. This trapped oxygen is exhausted while the hypoxic air is pumped into the semi-sealed enclosure to create the environment where there is less relative and absolute oxygen. Simulated altitudes of 14,500 feet can be achieved, and can be controlled to within 100 feet accuracy using CAT's proprietary digital control system. The digital controller stabilizes the altitude even when the environment changes and continuously monitors oxygen and $CO_2$ levels and temperature. Hypoxico's simulation is accomplished using a high-flow hypoxic air unit and a semi-sealed enclosure. The air unit works in a similar fashion as that described above. Simulated altitudes of about 21,500 feet can be achieved with this system. An alternative to this type of system is one which relies on merely blending nitrogen gas with ambient air to achieve the appropriate hypoxic conditions. Hypoxicator uses a semipermeable membrane to separate oxygen from air. The patient wears the device as a mask and breathes through the mask. Inspired air is reduced in oxygen content. This type of device offers the convenience that one is not confined to a hypoxic enclosure, but may continue to conduct normal routine activities while being exposed to the hypoxic condition. Because masks are easy to put on and take of, they are suitable for use in the EHT regimens as well as for use in the IHT regimens. The enclosure systems are really only suitable for use in EHT regimens. Still, while not preferred, one could set up two enclosure systems with an air lock between them in which one enclosure has a first hypoxic condition and the second has either a normoxic or a second hypoxic condition and the patient can move between the two enclosures in order to effect the IHT regimen or the EHT dual hypoxic condition regimen discussed above.

The second major component of the CAT system and the Hypoxico enclosure system is the hypoxic enclosure itself. The enclosure receives the hypoxic air from the air unit and contains it within a semi-sealed space. Hypoxic air is continuously pumped into the enclosure at rates as high as 150 liters/minute (in the CAT system) and as high as 120 l/min (in the Hypoxico enclosure system) to maintain the hypoxic environment. Because of the high flow through rates, carbon dioxide, heat, and humidity diffuse from the tent creating a comfortable environment within the enclosure. A low cost alternative with the use of the mere blending of nitrogen gas with the ambient air, is the use of a face mask and small portable nitrogen gas tanks with appropriate ambient air intake and mixing ability. This leaves the patient with greater mobility during treatment as the patient is not confined to the treatment enclosure.

Previous studies using athletes have varied significantly in the duration and degree of altitude exposure. Epogen blood levels increase 90-120 mins after a reduction in inspiratory $pO_2$ (23, 24) although the minimum duration required leading to an increase in red blood cell mass and volume is not well defined. Casas et al compared the efficacy of 3 differing altitude exposure protocols starting at 4000 m and gradually increasing by 500 m per session to 5,500 m. The 3 protocols were as follows: 17 consecutive days (3-4 hours per day), 9 consecutive days (3-4 hours per day), 9 alternate days (1.5 hours per day). They found that all three protocols produced a positive hematological adaptive response (increase in RBC count, packed cell volume and hemoglobin) (25). Ri-Li Ge et al demonstrated that altitude exposures of 2100-2500 m are required to produce a sustained epogen response and that exposure to lower altitudes (1700-2085 m) produce only a transient rise (24). Furthermore, studies of athletes "living high and training low" have shown that even moderate altitude exposure (2500 m) is sufficient to enhance performance (26).

The recommended use of the CAT system for "live high train low" is as follows: starting at a simulated altitude of 1500 m, simulated elevation is increased by 300 m each session to a maximal recommended altitude of 2700 m.

The recommended use of the Hypoxico system for "live high train low" is as follows: starting at a simulated altitude of 1500 m, simulated elevation is increased by 300 m each session to a maximal recommended altitude of 2700 m. In one preferred protocol of the invention, subjects follow the same acclimatization schedule. Subjects are exposed to 10 simulated altitude sessions spread out over 22 days. Where possible sessions take place on alternate weekdays (Monday, Wednesday, Friday). Variations on this schedule may be required to accommodate the needs of certain subjects. Each session should last 3-4 hours. Subjects are seated comfortably in the Hypoxico enclosure for the duration of the session. Oxygen saturation and heart rhythm are monitored (preferably continuously) and blood pressure monitored, preferably every 30 minutes. An independent oxygen sensor is preferably used to monitor the actual oxygen content in the altitude room. A session is terminated for any of the following reasons: shortness of breath, chest pain, dizziness, a sustained drop in oxygen saturation below 85%, hypotension, significant arrhythmia and a sustained increase in heart rate of more than 20%. Subjects may continue the protocol at the next scheduled session at the highest altitude tolerated during a prior session. If symptoms recur at a prior tolerated altitude the patient is withdrawn from the treatment. The foregoing, while a preferred protocol, is just that, a preferred protocol and many other variations on the theme will be apparent to those of ordinary skill in the art.

In one embodiment of the present invention exercise training is included in at least a portion of at least one of the normoxic periods during the IHT regimen or within 1 hour after the conclusion of either of the IHT or EHT regimens on any given day. In a second embodiment of the invention, exercise training is included during at least a portion of the hypoxic periods of the IHT and EHT regimens. The length of the training and the degree of training are generally adjusted (by the clinician administering the hypoxic treatment) to the patient and the patient's particular condition at the time of the training session.

Acetazolamide, a weak diuretic sometimes used for heart failure, is a carbonic anhydrase inhibitor that causes bicarbonate excretion. As a result, blood acidity increases, which serves as a stimulus to increase ventilation and thereby promoting adaptation to hypoxia. Basnyat et al showed that administering acetazolamide at a dose of 125 mg PO BID significantly reduced the incidence of acute mountain sickness (32). Other studies have demonstrated efficacy at this dose (34, 35, 36) and acetazolamide is approved for use for this indication. Furthermore, Jonk et al studied the effects of acetazolamide during hypoxic exercise (33). They demonstrated that acetazolamide did not affect $VO_2$, cardiac output, leg blood flow, or muscle gas exchange. As a result, acetazolamide is unlikely to mitigate the proposed beneficial effects of exposure to simulated high altitude in heart failure subjects.

Therefore, subjects in the foregoing treatments, are preferable given acetazolamide at a dose of 125 mg PO BID, preferably 48 hours prior to starting the acclimatization schedule and continue (as tolerated) for the duration of the sessions, Other dosing regimens of acetazolamide as are tolerated by the patient are acceptable as well. If subjects do not tolerate the acetazolamide, it can be dispensed with and the subject may continue the protocol as set forth without the use of acetazolamide. Without being bound to the theory, the inventors believe that the action of acetazolamide in this use is due to the carbonic anhydrase inhibition property and therefore other medically acceptable carbonic anhydrase inhibitors are acceptable alternatives for the acetazolamide in the context of the present invention.

EXAMPLES

The following non-limiting Examples are designed to exemplify, not limit, the scope of the invention, which is limited only by the claims appended hereto.

Example 1

A patient with chronic heart failure with exercise limitation undergoes EHT altitude treatment at escalating altitude starting at 1500 m increasing each session to a maximum 2500 m. Each session last 3 hours and session take please on alternate days. Treatment continues at 2500 m on alternate days for 3 months. Treatments are combined with an exercise training regimen.

Example 2

A patient with deconditioning after myocardial infarction undergoes EHT starting one month after the event. EHT sessions are as follows—Sessions are initiated starting at 1500 m increasing each session to a maximum of 2700 m. Each session lasts 1.5 hours and sessions take place each day. Treatment continues at 2700 m each day for 3 months. Treatments are combined with an exercise training regimen.

Example 3

A patient after a cardiothoracic surgical procedure undergoes EHT starting 2 weeks after surgery. Sessions are initiated starting at 1500 m increasing each session to a maximum 3000 m. Each session lasts 3 hours and sessions take place every other day. Treatment continues at 3000 m on alternate days for 3 months. Treatments are combined with an exercise training regimen.

Example 4

A patient with chronic heart failure with exercise limitation undergoes IHT at escalating altitude starting at 3,500 m increasing each session to a maximum 7,500 m. Each session last 1 hour having a five minute hypoxic period and a two minute normoxic period, with such cycles repeated for a total treatment session of 1 hour. Each individual session has all of its hypoxic components at a single altitude. Sessions take place twice a day for 1 month. Treatments are combined with an exercise training regimen as the patients condition improves.

Example 5

EHT conditions are achieved with the Colorado Attitude Training portable enclosure system or the HYPDXICO Altitude Training (HAT) Systems portable enclosure. Subjects are exposed to 10 altitude sessions over a period of 22 days. Each session lasts 3-4 hours with no ramp up period (i.e., patients are placed in the CAT or HAT system at the appropriate altitude setting directly from normal altitude for that patient). The initial session is at a simulated altitude setting of 1500 m and each subsequent session is increased in altitude simulation of 300 m up to a maximum of 2700 m. Comparison of the test results before and after the 10 session 22 day period, will show improvements in the patients condition which last a number of days after treatment termination.

Example 6-10

Examples 1-5 are repeated as above except exercise training is conducted during the normoxic conditions (in one or more of the intermediate normoxic periods of the intermittent hypoxic treatment or in the normoxic conditions within about 1 hour after conclusion of the extended hypoxic treatment or after the conclusion of the intermittent hypoxic treatment for that day).

Examples 11-15

Examples 1-5 are repeated except that the subjects undergoing the hypoxic treatment EHT or IHT engage in mild exercise training at the hypoxic conditions.

Examples 16-30

Examples 1-15 are repeated except that the subject is treated with 125 mg of acetazolamide twice daily beginning 48 hours before the first hypoxic treatment period.

References cited within the text above are as follows:
1. Levine B D, Stray-Gundersen J. "Living high-training low": effect of moderate altitude acclimatization with low altitude training on performance. Journal of American physiological society. 1997; 83(1)102-112.
2. Nummela A. Rusko H. Acclimatization to altitude and normoxic training improve 400-m running performance at sea level. *Journal of Sports Sciences.* 2000; 18(6):411-9.
3. Rankovic G, Radovanovic d. Physiological aspects of altitude training and the use of altitude simulators. Srpski Arhiv Za Celkupno Lekarstvo. 2005; 133(5-6):307-11. (Serbian abstract)
4. Heath D, Williams D R. *High-Altitude Medicine and Pathology.* 4$^{th}$ ed. New York, N.Y.: Oxford medical publications; 1995:68.
5. Hultgren H. High Altitude Medicine. Stanford California Hulgtren publications: 1997.
6. Navot-Mintzer D. Epstein M. Constantini N. Physical activity and training at high altitude. Harefuah. 142(10): 704-9, 2003(Abstract)
7. Liu Y. Steinacker J M. Dehnert C. Menold E. Baur S. Lormes W. Lehmann M. Effect of "living high-training low" on the cardiac functions at sea level *International Journal of Sports Medicine.* 1998; 19(6):380-4.
8. Kolar F. Ostadal B. Molecular mechanisms of cardiac protection by adaptation to chronic hypoxia. *Physiological Research.* 2004; 53 Suppl 1:S3-13.
9. Strniskova M. Ravingerova T. Neckar J. Kolar F. Pastorekova S. Barancik M. Changes in the expression and/or activation of regulatory proteins in rat hearts adapted to chronic hypoxia. *General Physiology & Biophysics.* 2006; 25(1):25-41.
10. Varosian M A. Kittnar O E. Prevention of heart failure by adapting the body to high-altitude hypoxia. *Patologicheskaia Fiziologiia i Eksperimentalnaia Terapiia.* 1991; (6): 41-3.
11. Clark A L, Poole-Wilson P A, Coats A J S. Exercise limitation in chronic heart failure: The central role of the periphery. J Am Col Cardiol 1996; 28:1092-1102.
12. Mancini D M, Henson D, LaManca J, Levine S. Evidence of reduced respiratory muscle endurance in patients with heart failure. J Am Coll Cardiol 1994; 24:972-981.
13. Lipkin D, Jones D, Round J, Poole-Wilson P. Abnormalities of skeletal muscle in patients with chronic heart failure. Int J Cardiol 1988; 18:187-195.
14. Donald S. Silverberg, Dov Wexler, Miriam Blum, Gad Keren, David Sheps, Eyal Leibovitch, David Brosh, Shlomo Laniado, Doron Schwartz, Tatyana Yachnin et al. The use of subcutaneous erythropoietin and intravenous iron for the treatment of the anemia of severe, resistant congestive heart failure improves cardiac and renal function and functional cardiac class, and markedly reduces hospitalizations. *Journal of the American College of Cardiology.* 2000; 35(7): 1737-1744.
15. Mancini D M. Katz S D. Lang C C. LaManca J. Hudaihed A. Androne A S. Effect of erythropoietin on exercise capacity in patients with moderate to severe chronic heart failure Circulation. 2003; 107(2):294-9.
16. Agostoni P. Cattadori G. Guazzi M. Bussotti M. Conca C. Lomanto M. Marenzi G. Guazzi M D. Effects of simulated altitude-induced hypoxia on exercise capacity in patients with chronic heart failure *American Journal of Medicine.* 2000; 109(6):450-5.
17. Erdmann J. Sun K T. Masar P. Niederhauser H. Effects of exposure to altitude on men with coronary artery disease and impaired left ventricular function. *American Journal of Cardiology.* 81(3):266-70, 1998.
18. Bernheim A. High altitude and cardiac disease. Schweiz Rundsch Med Prax. (German article) 2005; 94(45):1760-4.
19. Aerospace medical Association Medical guidelines Task Force, Alexandria, Va. Medical guidelines for airline travel. 2$^{nd}$ edition. Aviation, Space, and Environmental Medicine. 2003; 74(5):A1-A17.
20. Devereux R, Reichek N. Echocardiographic determination of left ventricular mass in man: anatomic validation of the method. Circulation 1977; 55:613-618.
21. Kolias T, Aaronson K, Armstrong W. Doppler-Derived dP/dt and −dP/dt Predict Survival in Congestive Heart Failure. JACC 2000; 36(5):1594-99.
22. Steele B: Timed walking tests of exercise capacity in chronic cardiopulmonary illness. J Cardiopulm Rehabil 1996; 16:25-33.
23. Richalet J P, Souberbielle J C, and Antezana A M. Control of erythropoiesis in humans during prolonged exposure to the altitude of 6,542 m. Am J Physiol Regulatory Integrative Comp Physiol. 1994; 266: R756-R764.
24. Ri-li Ge, S. Witkowski, Y. Zhang, C. Alfrey, M. Sivieri, T. Karlsen, G K. Resaland, M. Harber, J. Stray-Gunderson, and D. D. Levine. Determinants of erythropoietin release in response to short-term hypobaric hypoxia J Appl Physiol 2002; 92: 2361-2367.
25. H Casas, M Casas, A Ricart, R Rama, J Ibáñezl, L Palacios, F A. Rodríguez, J L Ventura, G Viscor and T Pagés. Effectiveness Of Three Short Intermittent Hypobaric Hypoxia Protocols: Hematological Responses Journal of Exercise Physiology. 2000; 3(2) 38-45.

26. B D. Levine Intermittent Hypoxic Training: Fact and Fancy. High Altitude Medicine & Biology 2002; 3(2): 177-193.
27. Brugniaux J V. Schmitt L. Robach P. Jeanvoine H. Zimmermann H. Nicolet G. Duvallet A. Fouillot J P. Richalet J P. Living high-training low: tolerance and acclimatization in elite endurance athletes. European Journal of Applied Physiology. 2006; 96(1):66-77.
28. Pyne D B, McDonald W A, Morton D S, Swigget J P, Foster M, Sonnenfeld G, Smith J A (2000) Inhibition of interferon, cytokine, and lymphocyte proliferative response in elite swimmers with altitude exposure. J Interferon Cytokine Res 20:411-41.
29. Groves B M. Reeves J T. Sutton J R. Wagner P D. Cymerman A. Malconian M K. Rock P B. Young P M. Houston C S. Operation Everest II: elevated high-altitude pulmonary resistance unresponsive to oxygen. *Journal of Applied Physiology.* 1987; 63(2):521-30.
30. Zielinski J. Effects of intermittent hypoxia on pulmonary hemodynamics: animal models versus studies in humans. *European Respiratory Journal.* 25(1): 173-80, 2005
31. M. R. Miller, J. Hankinson, V. Brusasco, F. Burgos, R. Casaburi, A. Coates, R. Crapo, P. Enright, C. P. M. van der Grinten, P. Gustafsson, R. Jensen, D. C. Johnson, N. MacIntyre, R. McKay, D. Navajas, O. F. Pedersen, R. Pellegrino, G. Viegi, and J. Wanger. Standardisation of spirometry. Eur. Respir. J. 2005; 26: 319-338.
32. Basnyat B, Gertsch J H, Johnson E W, Castro-Marin F, Inoue Y, Yeh C. Efficacy of low-dose acetazolamide (125 mg BID) for the prophylaxis of acute mountain sickness: a prospective, double-blind, randomized, placebo-controlled trial. High Alt med Biol. 2003; 4: 45-52.
33. Jonk A M, van den Berg, I P, Ifert I M, Wray D W, Arai T, Hopkins S R, Wagner P D. Effect of acetazolamide on pulmonary and muscle gas exchange during normoxic and hypoxic exercise. J Physiol. 2007; 579.3: 909-921.
34. Basnyat B, Gertsch J H, Holck P S, Johnson E W, Luks A M, Donham B P, Fleischman R J, Gowder D W, Hawksworth J S, Jensen B T, Kleiman R J, Loveridge A H, Lundeen E B, Newman S L, Noboa J A, Miegs D P, O'Beirne K A, Philpot K B, Schultz M N, Valente M C, Wiebers M R, Swenson E R. Acetazolamide 125 mg BD is not significantly different from 375 mg BD in the prevention of acute mountain sickness: the prophylactic acetazolamide dosage comparison for efficacy (PACE) trial. High Alt Med Biol. 2006; 7: 17-27.
35. Schoene, R B. Illnesses at High Altitude. Chest. 2008; 134: 402-416.
36. Tissot van Patot M C, Leadbetter III G, Keyes L E, Maakestad K M, Olson S, Hackett P H. Prophylactic Low-Dose Acetazolamide Reduces the Incidence and Severity of Acute Mountain Sickness. High Alt Med Biol. 2008; 9(4): 289-293.

I claim:

1. A method of treatment of a patient having a condition which limits exercise, said condition being selected from those conditions involving cardiac tissue, said treatment comprising administering to said patient an exercise limiting alleviating effective amount of normobaric hypoxic conditions (hypoxic treatment) said hypoxic conditions being extended hypoxic conditions for at least 1 hour per day without intermittent normoxic conditions (EHT), said treatment being for a treatment cycle of at least 1 day out of not more than 22 days per treatment cycle, said hypoxic conditions being an atmosphere having less than 20.9% oxygen content, said hypoxic conditions being administered for a time period of not more than a period equal to a day or a night in any one session, whereby said patient has fewer limits on exercise due to said condition after such administration than prior to said administration.

2. The method of claim 1 wherein said hypoxic conditions reduce inspired air oxygen content to not more than about 19%.

3. The method of claim 2 wherein said hypoxic conditions reduce inspired air oxygen content to not more than about 17%.

4. The method of claim 2 wherein said hypoxic conditions reduce inspired air oxygen content to not more than about 15%.

5. The method of claim 1 wherein said hypoxic conditions are maintained for at least 3 hours per day for at least 1 day out of not more than about every 22 days.

6. The method of claim 5 wherein said hypoxic treatment are maintained for at least 4 hours per day for at least 1 day out of not more than about every 22 days.

7. The method of claim 5 wherein said patient is exposed to said hypoxic conditions for at least 4 consecutive days out of not more than about every 22 days.

8. The method of claim 5 wherein said patient is exposed to said hypoxic treatment for at least 8 consecutive days out of not more than about every 22 days.

9. The method of claim 5 wherein said patient is exposed to said hypoxic treatment on approximately alternate days.

10. The method of claim 1 wherein a rest period of at least 6 days is introduced between treatment cycles.

11. A method of preventing congestive heart failure in a patient at risk thereof comprising administering to said patient an effective amount of normobaric hypoxic conditions (hypoxic treatment), said hypoxic conditions being extended hypoxic conditions for at least 1 hour per day without intermittent normoxic conditions (EHT), said treatment being for a treatment cycle of at least 1 day out of not more than 22 days per treatment cycle, said hypoxic conditions being an atmosphere having less than 20.9% oxygen content, said hypoxic conditions being administered for a time period of not more than a period equal to a day or a night in any one session, whereby said patient has a lesser risk of congestive heart failure after such administration than prior to said administration.

12. A method of improving cardio-pulmonary function in a patient suffering from or at risk of congestive heart failure, ventricular failure, angina, systolic heart failure, or diastolic heart failure comprising administering to said patient to a regimen of normobaric hypoxic conditions (hypoxic treatment), said hypoxic conditions being extended hypoxic conditions for at least 1 hour per day without intermittent normoxic conditions (EHT), said treatment being for a treatment cycle of at least 1 day out of not more than 22 days per treatment cycle, said hypoxic conditions being an atmosphere having less than 20.9% oxygen content, said hypoxic conditions being administered for a time period of not more than a period equal to a day or a night in any one session, whereby said patient has improved cardio-pulmonary function after such administration than prior to said administration.

13. The method of claim 1 wherein said hypoxic conditions include corresponding reductions in carbon dioxide content of said inspired air so that oxygen and carbon dioxide are in the same proportion to each other as in ambient air.

14. The method of claim 1 wherein said hypoxic condition is maintained by extracting at least a portion of the oxygen content of the air which is then supplied to said patient for inspiration.

15. The method of claim 1 wherein said hypoxic condition is maintained by adding nitrogen to ambient air to result in a lesser oxygen content air and supplying said lesser oxygen content air to said patient for inspiration.

16. The method of claim 1 wherein said patient has a cardiomyopic condition.

17. The method of claim 1 wherein said condition is recovery from a surgical procedure.

18. The method of claim 1 wherein said patient is treated with a carbonic anhydrase inhibitor at least concurrently with said hypoxic treatment.

19. The method of claim 18 wherein said carbonic anhydrase inhibitor treatment is begun at least 48 hours prior to initiating said hypoxic treatment.

20. The method of claim 18 wherein said carbonic anhydrase inhibitor is acetazolamide.

21. The method of claim 11 which further comprising
   (a) conducting exercise training under
      (i) said hypoxic periods of said treatment,
      (ii) normoxic conditions between two hypoxic conditions, or
      (iii) within an hour of termination of said hypoxic condition, or
   (b) treating said patient with a carbonic anhydrase inhibitor concurrently with said hypoxic treatment, or
   (c) both (a) and (b).

22. The method of claim 12 which further comprising
   (a) conducting exercise training under
      (i) said hypoxic periods of said treatment,
      (ii) normoxic conditions between two hypoxic conditions, or
      (iii) within an hour of termination of said hypoxic condition, or
   (b) treating said patient with a carbonic anhydrase inhibitor concurrently with said hypoxic treatment, or
   (c) both (a) and (b).

23. The method of claim 1 which further comprising
   (a) conducting exercise training under
      (i) said hypoxic periods of said treatment,
      (ii) normoxic conditions between two hypoxic conditions, or
      (iii) within an hour of termination of said hypoxic condition, or
   (b) treating said patient with a carbonic anhydrase inhibitor concurrently with said hypoxic treatment, or
   (c) both (a) and (b).

* * * * *